(12) United States Patent
Khalak et al.

(10) Patent No.: US 8,175,846 B2
(45) Date of Patent: May 8, 2012

(54) FAULT SPLITTING ALGORITHM

(75) Inventors: Asif Khalak, Phoenix, AZ (US); C. Arthur Dins, Minneapolis, MN (US); Bradley John Barton, Albuquerque, NM (US); Randy Magnuson, Scottsdale, AZ (US); Qingqiu Ginger Shao, Oro Valley, AZ (US); David Michael Kolbet, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 625 days.

(21) Appl. No.: 12/366,472

(22) Filed: Feb. 5, 2009

(65) Prior Publication Data

US 2010/0198610 A1  Aug. 5, 2010

(51) Int. Cl.
G06F 19/00  (2006.01)
(52) U.S. Cl. ............. 702/181; 702/183; 714/1
(58) Field of Classification Search ............ 702/35, 702/81, 115, 127, 179, 182, 183, 184, 185, 702/186, 188, 181; 705/2; 706/15, 20, 52; 714/1, 47.2
See application file for complete search history.

(56) References Cited

U.S. PATENT DOCUMENTS

| | | | |
|---|---|---|---|
| 5,465,321 | A | 11/1995 | Smyth |
| 5,661,668 | A | 8/1997 | Yemini et al. |
| 5,950,147 | A | 9/1999 | Sarangapani et al. |
| 5,987,399 | A | 11/1999 | Wegerich et al. |
| 6,119,111 | A | 9/2000 | Gross et al. |
| 6,353,815 | B1 | 3/2002 | Vilim et al. |
| 7,050,935 | B1 | 5/2006 | Draber |
| 7,080,290 | B2 | 7/2006 | James et al. |
| 7,539,597 | B2 * | 5/2009 | Wegerich et al. ............. 702/185 |
| 2004/0078171 | A1 | 4/2004 | Wegerich et al. |
| 2010/0088538 | A1 * | 4/2010 | Kolbet et al. ............. 714/1 |
| 2010/0198771 | A1 * | 8/2010 | Khalak et al. ............. 706/52 |

OTHER PUBLICATIONS

European Examination Report from corresponding EP Application No. 09 176 958.8, mailed Jul. 22, 2010, 8 pages.
European Search Report from corresponding EP Application No. 09 176 958.8, mailed Jul. 2, 2010, 2 pages.
H. Guo et al., "Automatic Creation of Markov Models for Reliability Assessment of Safety Instrumented Systems;" Reliability Engineering & System Safety, vol. 93, No. 6, Jun. 2008, pp. 807-815.
U.S. Appl. No. 12/366,475, titled "Method for Computing the Relative Likelihood of Failures," filed Feb. 5, 2009.
USPTO Office Action for U.S. Appl. No. 12/366,475; Notification Date Nov. 2, 2011.

* cited by examiner

*Primary Examiner* — John H Le
(74) *Attorney, Agent, or Firm* — Ingrassia Fisher & Lorenz, P.C.

(57) ABSTRACT

The present application relates to a method of splitting a fault condition including receiving evidence observations of a monitored system from monitors connected in a many-to-many relationship to the failure modes, generating a fault condition, computing a relative probability of failure for each failure mode in the fault condition. When there is more than one failure mode in the fault condition, the method includes computing a relative probability of each pair of failure modes in the fault condition, ranking the computed relative probabilities of the individual failure modes and the computed relative probabilities of the pairs of failure modes. If the highest ranked failure mode is a pair of failure modes, the fault condition is split based on the failure modes in the highest ranked pair of failure modes are split. If the highest ranked failure mode is an individual failure mode, a failure is isolated based on the ranking.

14 Claims, 3 Drawing Sheets

FAULT SPLITTING ALGORITHM

GOVERNMENT LICENSE RIGHTS

The U.S. Government may have certain rights in the present invention as provided for by the terms of Government Contract #W56HZV-05-C-0724 with the Army.

CROSS REFERENCE TO RELATED APPLICATIONS

This application is related to U.S. patent application Ser. No. 12/366,475 having a title of "A METHOD FOR COMPUTING THE RELATIVE LIKELIHOOD OF FAILURES" (also referred to here as the "H0020311-5548 Application") filed on the same date herewith. The H0020311-5548 application is hereby incorporated herein by reference.

BACKGROUND

In preventive maintenance and mission planning, it is important to calculate the likelihood of failures in a monitored system as symptoms (evidence) are observed. Since many failures frequently have overlapping evidence, it is often the case that ambiguity in fault reasoning will exist when trying to find the root cause failure.

In some currently available health management systems, all the evidence is collected in one big reasoning bucket and it is assumed that there is only one failure. In some cases, however, there are two or more failures in a monitored system. In this case, the health management system will only indicate a single failure.

Other currently available health management systems allow for any number of faults, however the computation is exponentially expensive.

SUMMARY

A method for splitting a fault condition based on a relative likelihood of the failure modes is provided. The method includes receiving evidence observations of a monitored system from monitors connected in a many-to-many relationship to the failure modes, generating a fault condition comprising states of all failure modes for a reference model of the monitored system based on the evidence observations, computing a relative probability of failure for each failure mode in the fault condition. When there is more than one failure mode in the fault condition, the method includes computing a relative probability of each pair of failure modes in the fault condition, ranking the computed relative probabilities of the individual failure modes and the computed relative probabilities of the pairs of failure modes. If the highest ranked failure mode is a pair of failure modes, the method includes splitting the fault condition based on the failure modes in the highest ranked pair of failure modes and, if the highest ranked failure mode is an individual failure mode, isolating a failure based on the ranking The computing of the relative probability is based on a false alarm probability, a detection probability, and a ratio of prior probabilities of a candidate hypothesis to a null hypothesis of no active failure modes.

DRAWINGS

In accordance with common practice, the various described features are not drawn to scale but are drawn to emphasize features relevant to the present invention. Like reference characters denote like elements throughout figures and text.

DETAILED DESCRIPTION

Figure 1:
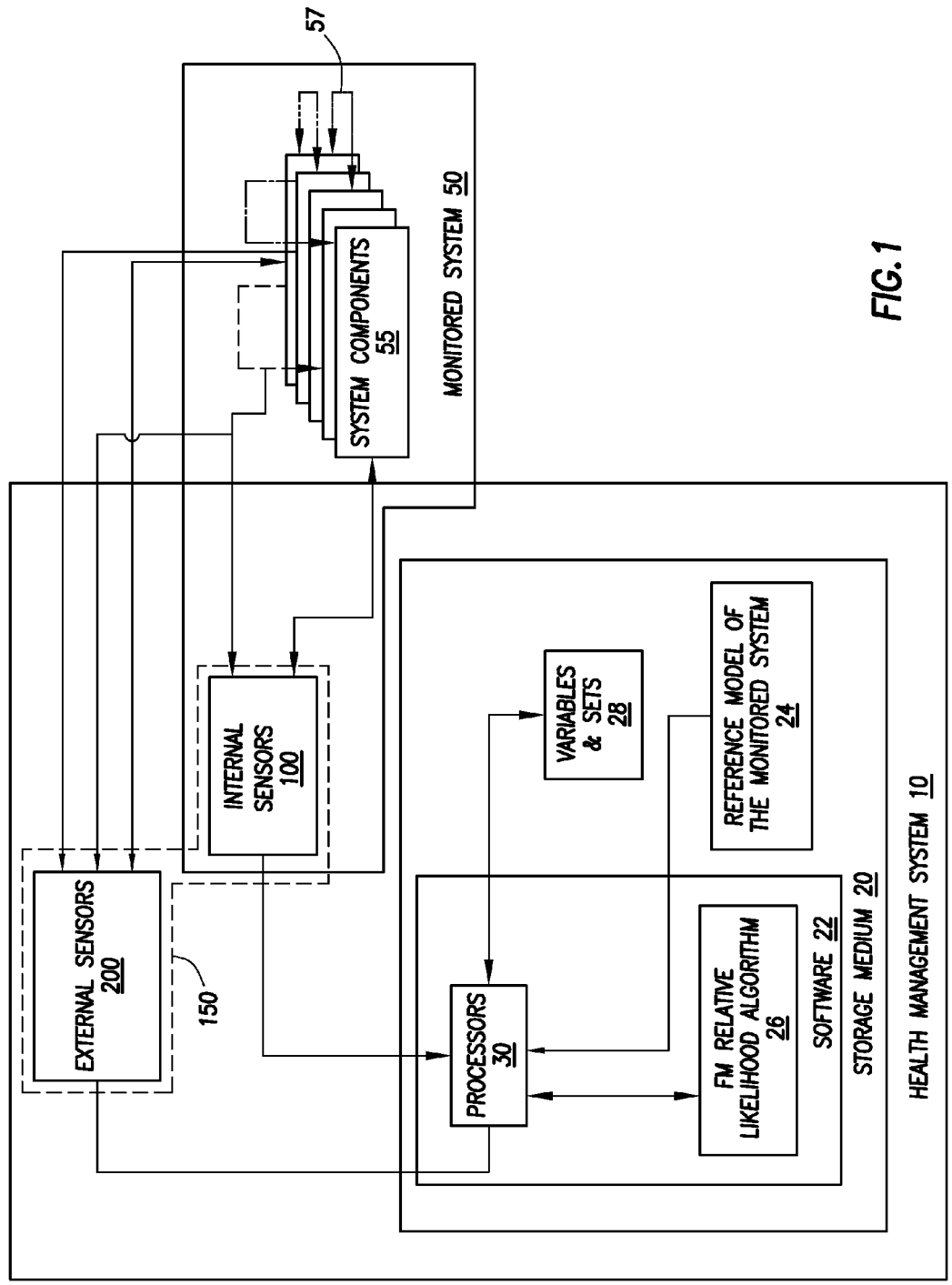
FIG. 1 is a block diagram of one embodiment of a health management system and a monitored system in accordance with the present invention.

In the following detailed description, reference is made to the accompanying drawings that form a part hereof, and in which is shown by way of illustration specific illustrative embodiments in which the invention may be practiced. These embodiments are described in sufficient detail to enable those skilled in the art to practice the invention, and it is to be understood that other embodiments may be utilized and that logical, mechanical and electrical changes may be made without departing from the scope of the present invention. The following detailed description is, therefore, not to be taken in a limiting sense.

In preventive maintenance and mission planning, it is important to calculate the likelihood of failures in the monitored system as symptoms (evidence) are observed. Since many failures frequently have overlapping evidence, there is often ambiguity in fault reasoning when trying to find the root cause of the failure. Moreover, an algorithm is needed to use the evidence observed and known system relationships to calculate a likelihood of a failure occurrence. The health management systems described herein implement a computationally inexpensive algorithm to determine if a monitored system is experiencing one or more failures. If more than one failure is being detected, each of the failures is isolated. This method provides isolation of failures physically present at the time of diagnosis.

The failure-mode-relative-likelihood algorithm described herein computes the probability of a hypothesized pattern of failure modes, given evidence observations, relative to a null hypothesis of no active failure modes. The failure-mode-relative-likelihood algorithm described herein solves a binary many-to-many probabilistic fault isolation problem in which many elements of evidence can suggest a single failure mode and conversely, each element of evidence can suggest multiple failure modes.

The failure-mode-relative-likelihood algorithm uses probability theory in a rigorous manner to resolve two primary complications of the reasoning tasks. First, the failure-mode-relative-likelihood algorithm resolves a situation in which there are many elements of evidence that suggest the same failure mode, but some of the elements are disagreeing. Second, the failure-mode-relative-likelihood algorithm is used to determine which failure mode was triggered when the elements of evidence suggest multiple failure modes.

When the probability that we are tracking more than one failure is greater than any one fault condition, the faults are split into two groups (islands of single fault assumption) in which it is assumed that each fault condition has only one active failure mode. In this manner, single fault reasoning is implemented to track more than one fault. The use of single fault reasoning (i.e., the failure-mode-relative-likelihood algorithm) keeps the computation and computation costs down.

The problem of fault condition splitting is divided into two steps; a fault condition is analyzed to determine if it should be split in order to maintain the single fault assumption; and two new fault conditions are created from the elements of the old fault condition. These steps are repeated until each new fault condition is tracking a single fault. The failure-mode-relative-likelihood algorithm determines the probability of a given hypothesis. The term "failure mode" is used to describe the actual fault that has occurred. If a fault condition has received no new evidence of a failure, there is no need to split the fault condition. When new evidence of a failure mode is received, the failure-mode-relative-likelihood algorithm determines if the fault condition should be split by: comparing 1) the relative likelihood that a given failure mode is active within a given fault condition with 2) the relative likelihood that more than one failure mode is present for a given fault condition. In all, when there are 'n' faults (n is an integer) in the fault condition, there are $n^2/(2+n)$ possibilities to be evaluated. The relative likelihoods are calculated for the failure modes in the fault condition and the most probable is selected. If the most probable case involves a pair of failure modes, then the fault condition is split into two fault conditions that each includes one of the two failure modes. The remaining failure modes in the original fault condition are allocated to one of the two new fault conditions based on the 'proximity' of the failure mode to the two failure modes. The metric to determine this proximity is represented by how strongly the failure mode is indicated by the same evidence as those related to the two failure modes that seed each of the new fault conditions. The distance metric is the dot product of the two detection probability vectors $d_{ik}$ for each failure mode. The distance metric is written as:

$$m(j, k) = \sum_i d_{ij} d_{ik},$$

where the metric is m, and the indices of the failure modes being compared are j and k and where $d_{ij}$ is the detection probability that evidence i detects a fault in the failure mode j.

In this manner, a distance metric determines which fault is associated with which fault condition in order to separate a multiple fault condition into the islands of single fault assumption. The failure-mode-relative-likelihood algorithm is a combination of Noisy-OR model and a naïve Bayesian reasoner. The failure-mode-relative-likelihood algorithm is in model-based software that uses a reference model of the monitored system, which is referred to herein as a vehicle.

The reference model of the vehicle (monitored system) models all critical aspects of the vehicle including the electronics, the physical structure of the parts of the vehicle, the connectivity between the parts of the vehicle, the function provided by each part of the vehicle, and the kinds of failures each part can experience. The model correlates information indicative of failures from sensors. The sensors are connected in a many-to-many relationship to the failure modes. The sensors are Boolean YES or NO (alternatively referred to as ON or OFF) monitors that output a binary indication of the state of the monitored aspect of the reference model. In this manner, the sensors provide a statement of evidence from a lower level component in the vehicle obtained during a built-in test of the components, parts, connections, etc. If a sensor is tripped, there is a condition of interest (e.g., the temperature is too high, a pressure on a part is too high, a connection between parts is broken, etc).

As defined herein, the "relative probability" is the probability normalized by the probability of a null hypothesis in which there are no active failure modes in the fault condition. The relative probability of a candidate hypothesis is used to determine a relative probability of a failure mode. Thus, the relative probability of a candidate hypothesis is the probability of the candidate hypothesis normalized by the probability of a null hypothesis. Likewise, the relative probability of a failure mode is the probability of the failure mode normalized by the probability of a null hypothesis. In one implementation of this embodiment, the monitored system is an aircraft. In another implementation of this embodiment, the monitored system is a land vehicle or water-based vehicle.

Table 1 shows the variables and datasets that define the problem.

TABLE 1

Names of variables and sets

| Name | Explanation |
| --- | --- |
| FC | Vector variable consisting of the states of all of the failure modes in an fault condition |
| $FM_i$ | Scalar variable associated with the (binary) state of a single $i^{th}$ failure mode |
| $M_i$ | Scalar variable associated with the (binary) state of the $i^{th}$ monitor |
| $M_{ik}'$ | (hidden) state of the $i^{th}$ monitor as it relates to the behavior of the $k^{th}$ failure mode |
| $d_{ik} =$ $p(M_{ik}' = 1 \| FM_k = 1)$ | Detection probability - probability that a $k^{th}$ failure mode will cause the $i^{th}$ monitor to trigger "TRUE" (i.e., "indicting") |
| $f_i$ | false alarm probability - probability that the $i^{th}$ monitor reads "TRUE" (i.e., "indicting") due to a false alarm |
| fc | Candidate hypothesis of an FC for analysis |
| $f_m^a$ | Special case of an FC in which $FM_a = 1$, and $FM_{b \neq a} = 0$ |
| $f_m^0$ | Special case of an FC in which $FM_i = 0$ for every i |
| R | Set of relevant monitors to the failure modes in FC |
| $F_i$ | Set of failure modes related to monitor $M_i$ |
| A | Set of active failure modes in FC |

As defined herein, a fault condition (FC) is a logical structure that includes all the failures considered to cause a part of the monitored system or connections between parts of the monitored system to fail. The fault condition is an array of failure modes that form an ambiguity group of failure modes. The relationship between failure modes and monitors is based on the manufacturing data. The manufacturing data is used to define the false alarm rate and the detection probability, which are then gradually built up over time by an implementation of a learning loop that updates the fault conditions for the hidden factor matrix. The learning loop is a case-based reasoning or fixed algorithm.

The prior art reasoning systems used to determine the probability of a failure mode assume the failure modes that contribute to the tripping of a particular monitor are known. However, there may be one or more failure modes that are not modeled or one or more environmental factors that are not modeled that could cause the monitor to trip. The failure-mode-relative-likelihood algorithm accounts for such unknown factors in a hidden state ($M_{ik}'$) of a monitor. As defined herein, the hidden state of a monitor ($M_{ik}'$) is an unknown external influence that may cause the monitor to behave the way it is behaving. The hidden state of a monitor is represented by the false alarm probability $f_i$, which is the probability that the $i^{th}$ monitor reads "TRUE" (i.e., "indicting") due to a false alarm. The detection probability $d_{ik}$ is the probability that a $k^{th}$ failure mode will cause the $i^{th}$ monitor to trigger "TRUE."

The failure-mode relative likelihood L(FC=fc|M) is the relative probability of a candidate hypothesis (fc), which includes the hypothetical state for each fault in the fault condition (FC), given the monitor readings (M). The monitor readings, M, refer to evidence observations of failure modes. The term "relative probability" means that the probability is normalized by the probability of the null hypothesis, fm$^0$, in which there are no active failure modes in the fault condition FC. Equation (1) shown below is the failure-mode-relative-likelihood algorithm, which describes the probability of the fault condition existing given that some of the monitors M are triggered or ON or TRUE.

$$L(FC = fc \mid M) = \frac{p(FC = fc)}{p(FC = fm^0)} \quad (1)$$

$$\prod_{\left\{i \left| \begin{matrix} M_i \in R \\ M_i = 1 \end{matrix} \right.\right\}} \left[ \frac{1 - (1 - f_i) \prod_{k \in A_i \cap F_i} (1 - d_{ik})}{f_i} \right] \prod_{\left\{i \left| \begin{matrix} M_i \in R \\ M_i = 1 \end{matrix} \right.\right\}} \left[ \prod_{k \in A \cap F_i} (1 - d_{ik}) \right]$$

The relative probability of a candidate hypothesis of the states of each fault in the fault condition, i.e., L(FC=fc|M), includes three factors: Pr, Tr, and Q.

$$Pr = \frac{p(FC = fc)}{p(FC = fm^0)}$$

and is the ratio of the prior probabilities of the candidate hypothesis, fc, to the null hypothesis, fm$^0$.

$$Q = \prod_{\left\{i \left| \begin{matrix} M_i \in R \\ M_i = 0 \end{matrix} \right.\right\}} \left[ \prod_{k \in A \cap F_i} (1 - d_{ik}) \right]$$

and is associated with the "quiescent" monitors in the fault condition ($M_i$=0). The "quiescent" or "untriggered" monitors are also defined herein as being OFF. The factor Q is the probability that the quiescent monitors originated from the candidate hypothesis normalized by the probability that the quiescent monitors resulted from the null hypothesis. In other words, the factor Q is the probability that the OFF monitors are expected to read OFF (i.e., "exonerating") when the hypothesis is true.

$$Tr = \prod_{\left\{i \left| \begin{matrix} M_i \in R \\ M_i = 1 \end{matrix} \right.\right\}} \left[ \frac{1 - (1 - f_i) \prod_{k \in A_i \cap F_i} (1 - d_{ik})}{f_i} \right]$$

and is associated with the "triggered" monitors in the fault condition ($M_i$=1). The "triggered" monitors are also defined herein as being ON. The factor Tr is the probability that the triggered monitors originated from the hypothesized fault condition normalized by the probability that the triggered monitors originated from the null hypothesis.

The factor Tr is a ratio of two probabilities, T1/T2, where:

$$T2 = \prod_{\left\{i \left| \begin{matrix} M_i \in R \\ M_i = 1 \end{matrix} \right.\right\}} f_i,$$

and is the probability that all of the "triggered" monitors are consistent with the null hypothesis (i.e., they are all false alarms).

$$T1 = \prod_{\left\{i \left| \begin{matrix} M_i \in R \\ M_i = 1 \end{matrix} \right.\right\}} 1 - (1 - f_i) \prod_{k \in A_i \cap F_i} (1 - d_{ik})$$

and is the probability that all of the "triggered" monitors are consistent with the candidate hypothesis, fc. That is, all the "triggered" monitors are triggered by failure modes in the candidate hypothesis.

FIG. 1 is a block diagram of one embodiment of a health management system 10 monitoring a monitored system 50 in accordance with the present invention. The monitored system 50 includes at least one system component 55, and internal sensors 100, also referred to herein as monitors 100. The health management system 10 includes sensors represented generally at 150, at least one processor 30, and a storage medium 20 to store software 22 executable by the at least one processor 30. The sensors 150 include both the internal sensors 100 in the monitored system 50, and external sensors 200, which are external to the monitored system 50. The health management system 10 is configured to determine relative probabilities of failure in a monitored system 50. The at least one processor 30 is referred to herein as the processors 30. The sensors 150, internal sensors 100, and external sensors 200 are also referred to herein as monitors 150, internal monitors 100, and external monitors 200, respectively.

Some of the system components 55 are connected to others of the system components 55 via connections represented generally at 57. The connections can be wired or wireless. The sensors 150 are communicatively coupled to the system components 55 to monitor the system components 55. Likewise, the sensors 150 are communicatively coupled to each of the connections 57 between the various system components 55 to monitor the linking between two system components. In one implementation of this embodiment, the sensors 150 also monitor the environment of the monitored system 50.

The sensors 150 are communicatively coupled to output evidence observations that are generated during the monitoring to the processors 30. The processors 30 received the evidence observations from the sensors 150. The processors 30 generate an array of failure modes that form the ambiguity group of failure modes based on the evidence observations received from the sensors 150. The processors 30 also execute algorithms in the software 22 configured to generate information regarding unknown causes of failures.

The software 22 stored in the storage medium 20 includes a failure-mode-relative-likelihood algorithm 26 stored in the storage medium 20. As shown in FIG. 1, the processors are in the software 22. The failure-mode-relative-likelihood algorithm 26 (shown above as equation (1)) is a combination of noisy-OR models and a naïve Bayesian reasoner. A reference model of the monitored system 24 is stored in the storage medium 20. In one implementation of this embodiment, the storage medium also stores variables and sets 28 generated by the processors 30. For example, the scalar and vector variables 28 shown in Table 1 are stored in the storage medium 20.

In one implementation of this embodiment, the monitored system 50 is an aircraft. In another implementation of this embodiment, the monitored system is a land vehicle. The processors 30 execute software 22 and/or firmware that causes the processors 30 to perform at least some of the processing described here as being performed by the health management system 10. At least a portion of such software 22 and/or firmware executed by the processors 30 and any related data structures are stored in storage medium 20 during execution. In one implementation of this embodiment, the processors 30 include a memory (not shown) that comprises any suitable memory now known or later developed such as, for example, random access memory (RAM), read only memory (ROM), and/or registers within the processors 30. In one implementation, the processors 30 comprise microprocessors or microcontrollers. The software 22 and/or firmware executed by the processors 30 comprises a plurality of program instructions that are stored or otherwise embodied on a storage medium 20 from which at least a portion of such program instructions are read for execution by the processors 30. In one implementation, the processors 30 comprise processor support chips and/or system support chips such as application-specific integrated circuits (ASICs).

Figure 2:
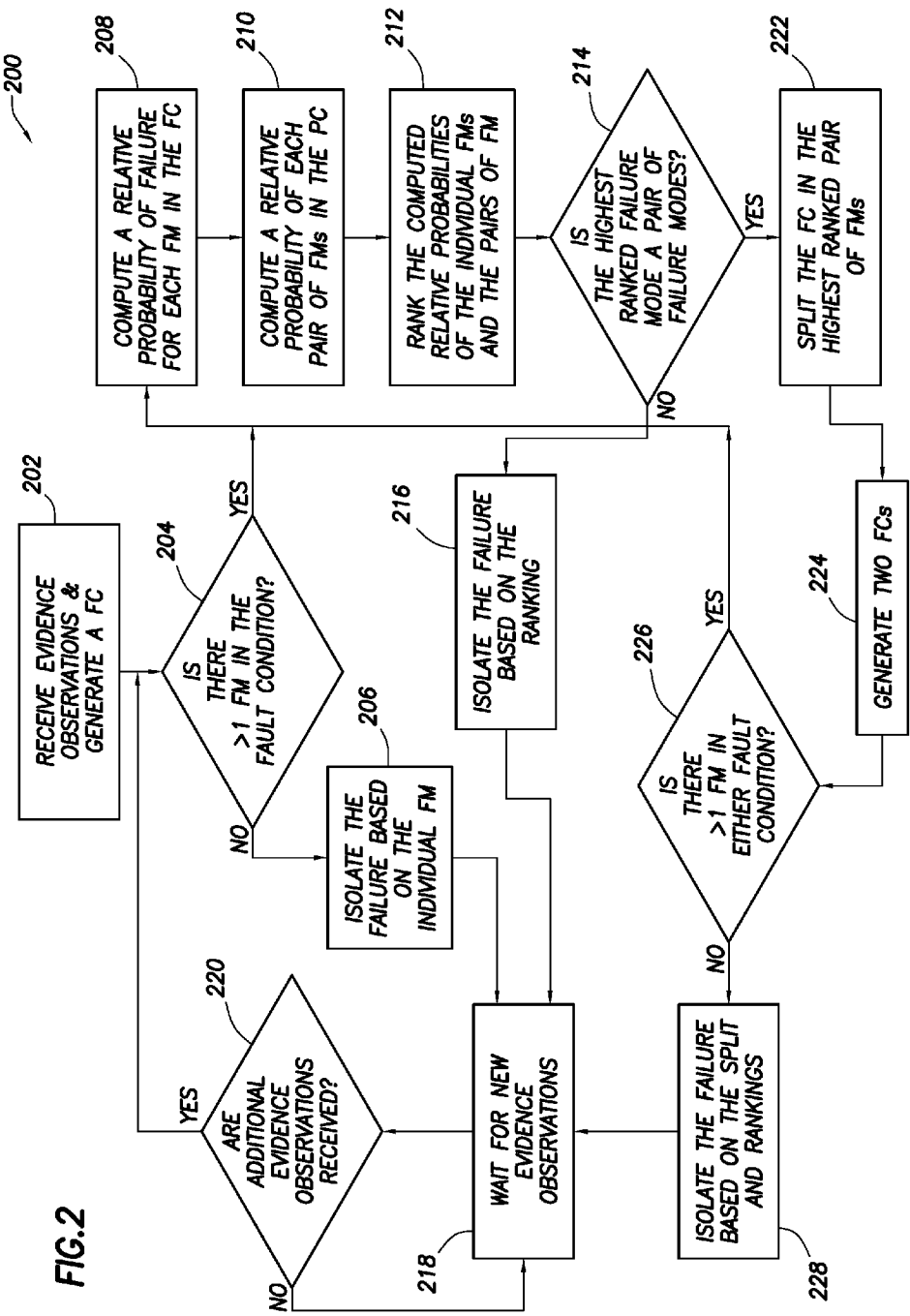
FIG. 2 is a flow diagram of an embodiment of a method for splitting a fault condition based on a relative likelihood of the failure modes in accordance with the present invention.

FIG. 2 is a flow diagram of an embodiment of a method 200 for splitting a fault condition based on a relative likelihood of the failure modes in accordance with the present invention. In one embodiment, the method 200 is implemented by the health management system 10 to monitor the monitored system 50 shown in FIG. 1 although it is to be understood that method 200 can be implemented using other embodiments of the monitored system 50 and the health management system 10 as is understandable by one skilled in the art who reads this document.

At block 202, evidence observations of a monitored system 50 are received from monitors 150 connected in a many-to-many relationship to the failure modes and a fault condition comprising states of all failure modes for a reference model of the monitored system is generated based on the evidence observations.

At block 204, the processors 30 determine if there is more than one failure mode in the generated fault condition. If there is not more than one failure mode in the fault condition, that failure mode is an individual failure mode and the flow proceeds to block 206. At block 206, the failure is isolated based on the individual failure mode and the flow proceeds to block 218. At block 218, the processors 30 wait for new evidence observations to be received from the sensors 150 of the monitored system 50.

If there is more than one failure mode in the fault condition, the flow proceeds from block 204 to block 208. At block 208, the processors 30 compute a relative probability of failure for each failure mode in the fault condition. The relative probability for each failure mode in the fault condition is based on a false alarm probability, a detection probability, and a ratio of prior probabilities of a candidate hypothesis to a null hypothesis of no active failure modes as described above.

At block 210, the processors 30 compute a relative probability of failure for each pair of failure modes in the fault condition. The relative probability for each pair of failure modes in the fault condition is based on a false alarm probability, a detection probability, and a ratio of prior probabilities of a candidate hypothesis to a null hypothesis of no active failure modes.

At block 212, the processors 30 rank the computed relative probabilities of the individual failure modes and the computed relative probabilities of the pairs of failure modes. At block 214, the processors determine if the highest ranked failure mode (i.e., the most probable failure mode) is a pair of failure modes. If the highest ranked failure mode is an individual failure mode, the flow proceeds to block 216. At block 216, the processors 30 isolate the failure based on the ranking done at block 212. The failure mode having the highest relative probability is indicative of the fault in the monitored system 50. At block 218, the processors 30 wait for new evidence observations to be received from the sensors 150 of the monitored system 50.

If the highest ranked failure mode is a pair of failure modes, the flow proceeds from block 214 to block 222. At block 222, the processors 30 split the fault condition based on the fault modes in the highest ranked pair of failure modes. At block 224, the processors generate two fault conditions for each of the failure modes in the pair of failure modes that were split. The processors 30 generate a first fault condition (FC1) for states of failure modes for a reference model of a monitored system based on a first failure mode in the pair of failure modes, and generate a second fault condition (FC2) for states of failure modes for the reference model of the monitored system based on the second failure mode in the pair of failure modes. The method for generating the first and second fault conditions is described below in detail with reference to method 300 of FIG. 3.

At block 226, the processors 30 determine if the first fault condition and/or the second fault condition have more than one failure mode. If there is more than one failure mode in either one or both of the first fault condition or the second fault condition, then the flow for the fault condition with two or more failure modes proceeds to block 208 and the flow from block 208 to block 224 or from block 208 to block 218 is repeated.

If there is not more than one failure mode in either one of the first fault condition or the second fault condition, then the flow for that fault condition with only one failure mode proceeds to block 228. At block 228, the processors 30 isolate the failure for the failure mode based on the split made at block 222 and based on the rankings done at block 212. From block 228 the flow proceeds to block 218 and the processors 30 wait for new evidence observations to be received from the sensors 150 of the monitored system 50. The system 10 remains in wait-mode as the processors 30 check for receipt of additional evidence observations at block 220. The method 200 loops between block 218 and block 220 until additional evidence observations are received. When additional evidence observations are received, the flow proceeds to block 204 and the process is repeated. In one implementation of this embodiment, the flow of method 200 continues until the health management system 10 is shut down or until the monitored system is turned off. Then the flow begins again from block 202 when the health management system 10 and/or monitored system are turned back on.

Figure 3:
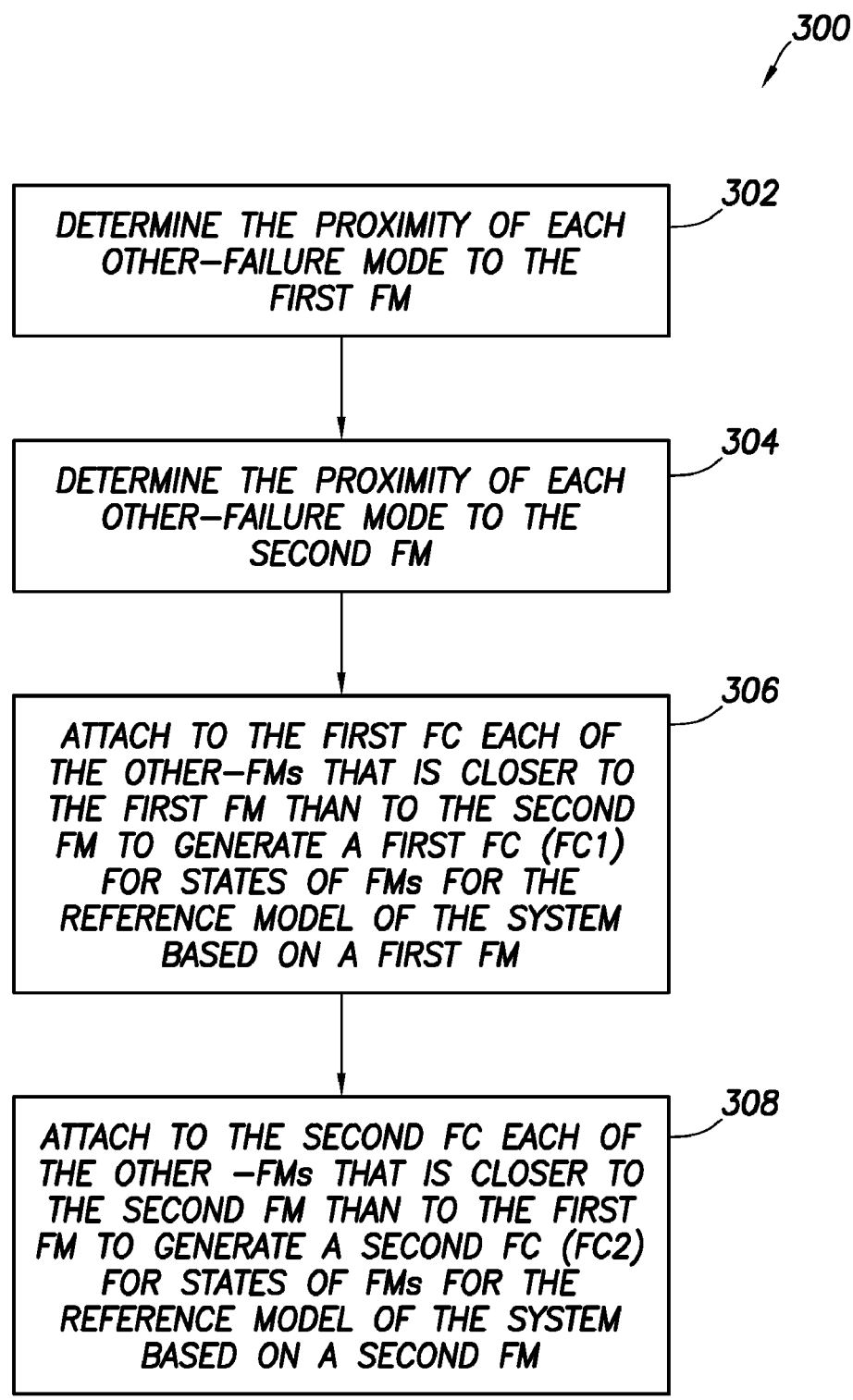
FIG. 3 is a flow diagram of an embodiment of a method for generating a first fault condition and generating a second fault condition in accordance with the present invention.

FIG. 3 is a flow diagram of an embodiment of a method 300 for generating a first fault condition and generating a second fault condition in accordance with the present invention. The first fault condition and second fault condition are generated when the highest rank failure mode is a pair of failure modes. In one embodiment, the method 300 is implemented by the health management system 10 while monitoring the monitored system 50 shown in FIG. 1 although it is to be understood that method 300 can be implemented using other embodiments of the monitored system 50 and the health management system 10 as is understandable by one skilled in the art who reads this document.

At block 302, the processors 30 determine the proximity of each other-failure mode to the first failure mode. As described above, the metric to determine the proximity is based on the distance metric, which is the dot product of the two detection probability vectors $d_{ik}$ for each failure mode. As defined herein, the failure modes in the fault condition include a first failure mode (a first one of the failure modes in the pair of failure modes that was ranked with highest relative probability), a second failure mode (a second one of the failure modes in the pair of failure modes that was ranked with highest relative probability), and other-failure modes that were in the fault condition. As defined herein, an "other-failure mode" is a failure mode in the fault condition that was not in the pair of failure modes that was ranked with highest relative probability.

At block 304, the processors 30 determine the proximity of each other-failure mode, other than the first failure mode and the second failure mode, to the second failure mode based on the distance metric.

At block 306, the processors 30 attach to the first fault condition each of the other-failure modes that is closer to the first failure mode than to the second failure mode to generate a first fault condition for the states of failure modes for the reference model of the system based on the first failure mode. At block 308, the processors 30 attach to the second fault condition each of the other-failure modes that is closer to the second failure mode than to the first failure mode to generate a second fault condition for the states of failure modes for the reference model of the system based on the second failure mode.

In this manner, the other-failure modes in the original fault condition are allocated to one of the two new fault conditions based on the 'proximity' of the failure mode to the two failure modes. Likewise, if the flow in method 200 is proceeds from block 226 to block 208, as described above with reference to FIG. 2, then the other-failure modes in the first and/or second fault condition are allocated to one of the two new fault conditions (e.g., a third and a fourth fault condition).

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

We claim:

1. A method for splitting a fault condition based on a relative likelihood of the failure modes, the method comprising:

receiving, in a processor, evidence observations of a monitored system from monitors connected in a many-to-many relationship to the failure modes; and in the processor:

generating a fault condition comprising states of all failure modes for a reference model of the monitored system based on the evidence observations;

computing a relative probability of failure for each failure mode in the fault condition, the relative probability being based on a false alarm probability, a detection probability, and a ratio of prior probabilities of a candidate hypothesis to a null hypothesis of no active failure modes;

when there is more than one failure mode in the fault condition, computing a relative probability of each pair of failure modes in the fault condition, the relative probability being based on a false alarm probability, a detection probability, and a ratio of prior probabilities of a candidate hypothesis to a null hypothesis of no active failure modes;

ranking the computed relative probabilities of the individual failure modes and the computed relative probabilities of the pairs of failure modes;

if the highest ranked failure mode is a pair of failure modes, splitting the fault condition based on the failure modes in the highest ranked pair of failure modes; and if the highest ranked failure mode is an individual failure mode, isolating a failure based on the ranking.

2. The method of claim 1, wherein splitting the fault condition comprises:

generating a first fault condition for states of failure modes for a reference model of a monitored system based on a first failure mode; and generating a second fault condition for states of failure modes for the reference model of the monitored system based on a second failure mode.

3. The method of claim 2, wherein generating a first fault condition and generating a second fault condition comprises:

determining the proximity of each other-failure mode to the first failure mode;

determining the proximity of each other-failure mode to the second failure mode;

attaching to the first fault condition each of the other-failure modes that is closer to the first failure mode than to the second failure mode; and attaching to the second fault condition each of the other-failure modes that is closer to the second failure mode than to the first failure mode.

4. The method of claim 2, further comprising:

computing a relative probability of failure for each failure mode in the first fault condition;

when there is more than one failure mode in the first fault condition, computing a relative probability of each pair of failure modes in the first fault condition;

ranking the computed relative probabilities of the individual failure modes in the first fault condition and the computed relative probabilities of the pairs of failure modes in the first fault condition;

if the highest ranked failure mode in the first fault condition is a pair of failure modes, splitting the first fault condition based on the failure modes in the highest ranked pair of failure modes in the first fault condition; and if the highest ranked failure mode in the first fault condition is an individual failure mode, isolating a failure based on a ranking of the relative probability of failure for each failure mode in the first fault condition.

5. The method of claim 4, further comprising:

computing a relative probability of failure for each failure mode in the second fault condition;

when there is more than one failure mode in the second fault condition, computing a relative probability of each pair of failure modes in the second fault condition;

ranking the computed relative probabilities of the individual failure modes in the second fault condition and the computed relative probabilities of the pairs of failure modes in the second fault condition;

if the highest ranked failure mode in the second fault condition is a pair of failure modes, splitting the second fault condition based on the failure modes in the highest ranked pair of failure modes in the second fault condition; and if the highest ranked failure mode in the second fault condition is an individual failure mode, isolating a failure based on a ranking of the relative probability of failure for each failure mode in the second fault condition.

6. The method of claim 1, further comprising:
receiving additional evidence observations of the monitored system from the monitors;
generating an updated fault condition for the states of failure modes for the reference model of the monitored system, the updated fault condition being based on the additional evidence observations received from the monitors;
computing a relative probability of failure for each failure mode in the updated fault condition;
when there is more than one failure mode in the updated fault condition, compute a relative probability of each pair of failure modes in the updated fault condition;
ranking the computed relative probabilities of the individual failure modes and the relative probabilities of the pairs of failure modes; and
splitting the fault condition based on the failure modes if the highest ranked failure mode is a pair of failure modes.

7. The method of claim 1, further comprising:
generating a ratio of the prior probabilities of the hypothesis to the null hypothesis;
generating a trigger factor associated with triggered monitors in the fault condition;
generating a quiescent factor associated with quiescent monitors in the fault condition; and
determining the relative probability from the ratio of the prior probabilities of the hypothesis to the null hypothesis, the trigger factor and the quiescent factor.

8. The method of claim 7, wherein generating the trigger factor associated with the triggered monitors in the fault condition comprises:
generating a probability for each monitor that the monitor reads TRUE due to a false alarm; and
generating a probability for each monitor to read TRUE due to a failure, the probability being generated for every failure mode in the fault condition.

9. The method of claim 1, wherein generating the quiescent factor associated with the quiescent monitors in the fault condition comprises:
generating a probability for each monitor to read TRUE due to a failure, the probability being generated for every failure mode in the fault condition.

10. The method of claim 1, further comprising:
generating the reference model of the monitored system; and
implementing Model-based software to generate the fault condition for the states-of-failure modes for the reference model of the monitored system.

11. A health management system configured to split a fault condition based on a relative likelihood of a failure mode in a monitored system, the health management system comprising:
sensors to detect system states and to output evidence observations;
at least one processor; and
a storage medium to store software executable by the at least one processor,
the at least one processor configured to:
generate a fault condition including states of all failure modes that are connected to the monitors based on the evidence observations received from the sensors for a reference model of the monitored system;
execute algorithms configured to compute a relative probability of failure for each failure mode based on a false alarm probability, a detection probability, and a ratio of prior probabilities of a candidate hypothesis to a null hypothesis of no active failure modes; and
split the fault condition when additional evidence is received to indicate that a given fault condition includes two failure modes by:
ranking the computed relative probabilities of the individual failure modes and the computed relative probabilities of the pairs of failure modes;
if the highest ranked failure mode is a pair of failure modes, split the fault condition based on the failure modes in the highest ranked pair of failure modes; and
if the highest ranked failure mode is the individual failure mode, isolate a failure based on the ranking.

12. The health management system of claim 11, wherein the monitored system includes system components, wherein at least one system component is communicatively coupled to at least one other system component, and wherein the sensors are configured to monitor the system components and the linking between two system components.

13. The health management system of claim 11, further comprising a failure-mode-relative-likelihood algorithm stored in the storage medium.

14. The health management system of claim 11, further comprising a reference model of the monitored system stored in the storage medium.

* * * * *